US010743486B2

(12) United States Patent
Weissmann et al.

(10) Patent No.: US 10,743,486 B2
(45) Date of Patent: Aug. 18, 2020

(54) METHODS OF SEPARATING HYBRID SEED FROM A MIXTURE OF SEEDS

(71) Applicant: BASF SE, Ludwigshafen am Rhein (DE)

(72) Inventors: Sigrid Weissmann, Bohlingen (DE); Elmar Alfons Weissmann, Bohlingen (DE); John Jacobs, Merelbeke (NL)

(73) Assignee: BASF SE, Ludwigshafen am Rhein (DE)

( * ) Notice: Subject to any disclaimer, the term of this patent is extended or adjusted under 35 U.S.C. 154(b) by 3 days.

(21) Appl. No.: 16/018,103

(22) Filed: Jun. 26, 2018

(65) Prior Publication Data

US 2018/0303052 A1  Oct. 25, 2018

Related U.S. Application Data

(63) Continuation of application No. 14/772,518, filed as application No. PCT/EP2014/055249 on Mar. 17, 2014, now Pat. No. 10,028,460.

(30) Foreign Application Priority Data

Mar. 18, 2013  (EP) .................................... 13159765

(51) Int. Cl.
*A01H 1/04* (2006.01)
*A01H 6/46* (2018.01)
*A01H 1/02* (2006.01)
*B07C 5/04* (2006.01)
*B07C 5/16* (2006.01)
*A01H 5/10* (2018.01)
*B07C 5/34* (2006.01)

(52) U.S. Cl.
CPC ................. *A01H 1/04* (2013.01); *A01H 1/02* (2013.01); *A01H 5/10* (2013.01); *A01H 6/4678* (2018.05); *B07C 5/34* (2013.01); *B07C 5/04* (2013.01); *B07C 5/16* (2013.01)

(58) Field of Classification Search
None
See application file for complete search history.

(56) References Cited

U.S. PATENT DOCUMENTS

| 3,842,538 A | 10/1974 | Barabas |
| 6,005,167 A | 12/1999 | Van Tunen et al. |
| 2011/0232247 A1 | 9/2011 | Zhu et al. |

FOREIGN PATENT DOCUMENTS

| CN | 1442038 A | 9/2003 |
| CN | 102475055 A | 5/2012 |
| CN | 102948361 A | 3/2013 |
| WO | 93/13649 A1 | 7/1993 |
| WO | 2012/038350 A1 | 3/2012 |

OTHER PUBLICATIONS

Hossain and Driscoll. Canadian Journal of Genetics and Cytology 23: 493-496 (1981).*
Zhou et al. Crop Science 46(1): 250-255 (2006).*
Li et al. Z. Planzenzuchtg. 90: 265-272 (1983).*
International Search Report and Written Opinion of the International Searching Authority, International Patent Application No. PCT/EP2014/055249, dated Apr. 23, 2014, 12 pages.
Foster, S., et al., "Discrimination of Alleles and Copy Numbers at the Q Locus in Hexaploid Wheat Using Quantitative Pyrosequencing", Euphytica, Oct. 2011, vol. 186, No. 1, pp. 207-218.
Jantasuriyarat C., et al., "Identification and Mapping of Genetic Loci Affecting the Free-Threshing Habit and Spike Compactness in Wheat (*Triticum aestivum* L.)", Theoretical and Applied Genetics, Jan. 2004, vol. 108, No. 2, pp. 261-273.
Nalam, V.J., et al., "Map-Based Analysis of Genetic Loci on Chromosome 2D that Affect Glume Tenacity and Threshability, Components of the Free-Threshing Habit in Common Wheat (*Triticum aestivum* L.)", Theoretical and Applied Genetics; International Journal of Plant Breeding Research, Oct. 2, 2007, vol. 116, No. 1, pp. 135-145.
Simonetti M.C., et al., "Quantitative Trait Loci Influencing Free-threshing Habit in Tetraploid Wheats", Genetic Resources and Crop Evolution, Jun. 1999, vol. 46, No. 3, pp. 267-271.
Simons, K.J., et al., "Molecular Characterization of the Major Wheat Domestication Gene Q," Genetics, Jan. 2006 ,vol. 172, No. 1, pp. 547-555.
Soods S., et al., "The Major Threshability Genes Soft Glume (sog) and Tenacious Glume (Tg), of Diploid and Polyploid Wheat, Trace Their Origin to Independent Mutations at Non-orthologous Loci," Theoretical and Applied Genetics, Jul. 2009, vol. 119, No. 2, pp. 341-351.
Wilson, P. and Driscoll, C.J., Heterosis: Reappraisal of Theory and Practice, Chapter 4, "Hybrid Wheat": pp. 94-123, Frankel et al, e4ds., Springer-Verlag (1983).
Driscoll, C.J., Crop Science 17:190, (1977).
Zheng, et al., Euphytica, 152:51-60, (2006).

* cited by examiner

*Primary Examiner* — David T Fox
(74) *Attorney, Agent, or Firm* — Arent Fox LLP

(57) ABSTRACT

The present invention relates to methods for separating hybrid seed from a mixture of hybrid seed and inbred seed. In particular, said hybrid seed and said inbred seed have different phenotypes allowing separation of said hybrid seed with non-invasive methods based on the differences in said phenotypes.

16 Claims, 7 Drawing Sheets

Non-free threshing

Free threshing

Wheat & oats

Barley

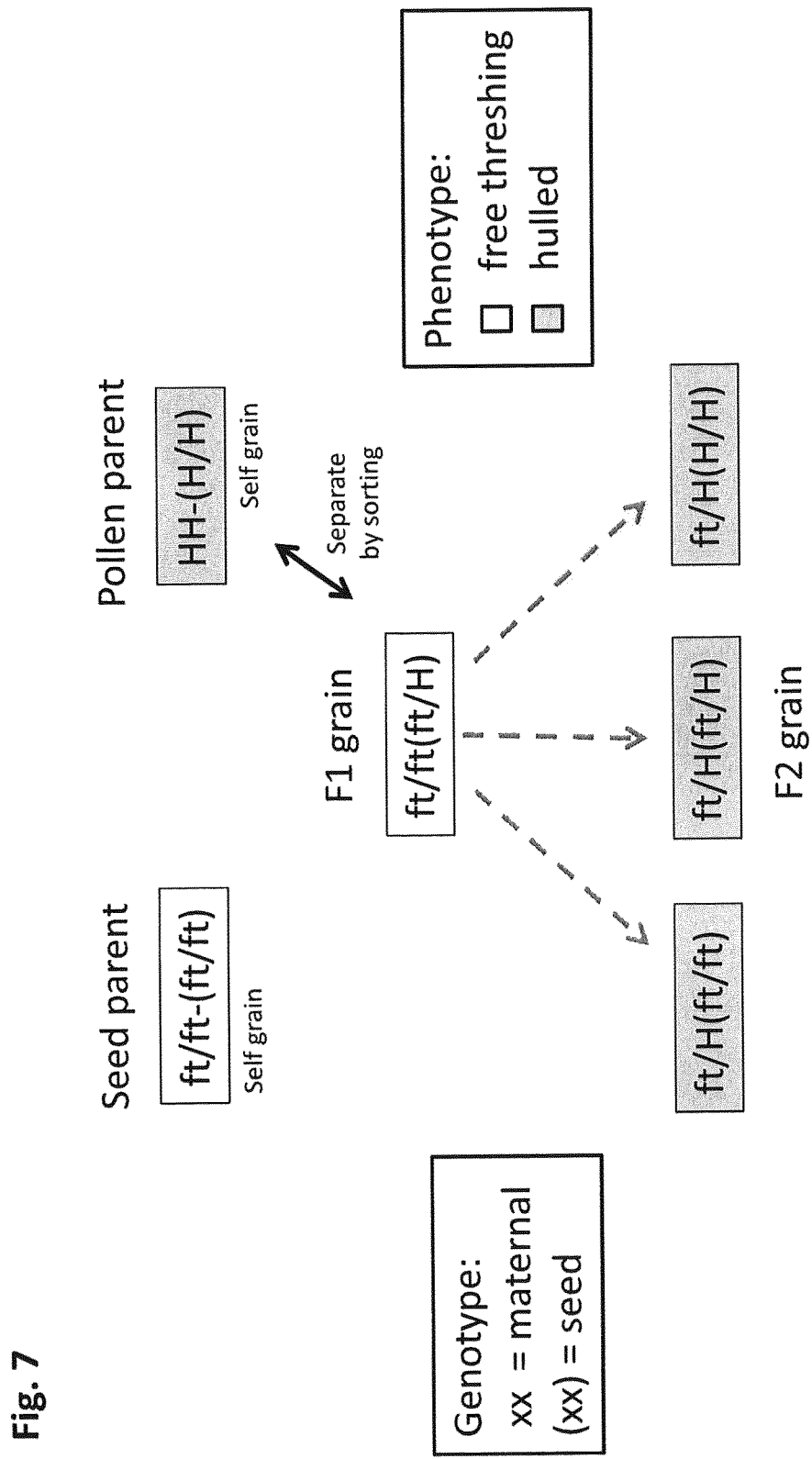

METHODS OF SEPARATING HYBRID SEED FROM A MIXTURE OF SEEDS

CROSS-REFERENCE TO RELATED APPLICATION(S)

Figure 1:
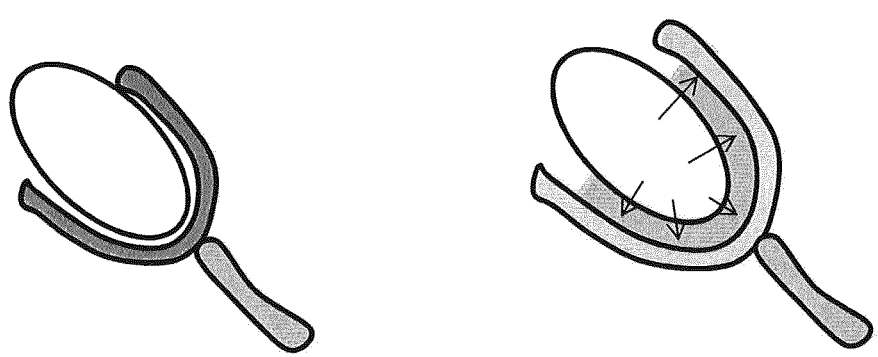
Figure 1:
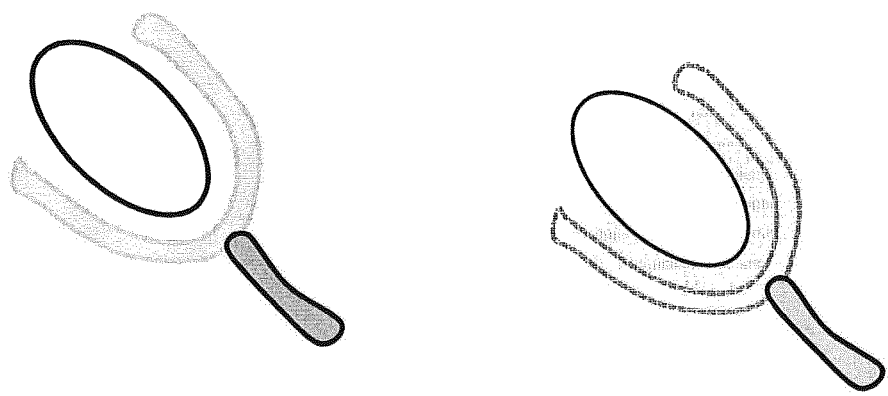

The present application is a continuation application of a 371 national stage application Ser. No. 14/772,518, filed Sep. 3, 2015, now U.S. Pat. No. 10,028,460, which claims the benefit of PCT International Application Serial No. PCT/EP2014/055249, filed on Mar. 17, 2014, which claims priority to European Patent Application No. 13159765.0, filed on Mar. 18, 2013, each of which is hereby incorporated by reference in its entirety. Applicant claims priority to each of the foregoing patent applications. The PCT International Application was published in the English language.

The present invention relates to the field of agriculture, more particular hybrid seed production and separation of hybrid seed from a seed mixture using separation methods based on differences in the phenotype of the seeds comprised in said seed mixture. Separation of hybrid seeds takes place based on e.g. differences in size, surface condition or specific weight of the hybrid seeds as compared to other seeds comprised in the mixture, e.g. inbred seeds.

Hybrid plants are bred to improve the characteristics of the resulting plants, such as better yield or yield stability, greater uniformity, improved color, disease resistance, etc. Today, hybrid seed production is predominant in agriculture and home gardening, and is one of the main contributing factors to the dramatic rise in agricultural output during the last half of the 20th century. In the US, the commercial hybrid seed market was launched in the 1920s, with the first hybrid maize. All of the hybrid seeds planted by the farmer will be the same hybrid while the seeds from the hybrids planted will not consistently have the desired characteristics.

Heterosis, or hybrid vigor (as in the familiar F1 hybrids of maize), occurs in common (hexaploid) wheat, but it is difficult to produce seed of hybrid cultivars on a commercial scale (as is done with maize) because wheat flowers are bi-sexual and normally self-pollinate. Commercial hybrid wheat seed has been produced using chemical hybridizing agents; these chemicals selectively interfere with pollen development, or naturally occurring cytoplasmic male sterility systems.

Hybrid plants are created by crossing a pollen parent to a seed parent of a different line or cultivar. In most cases, the male fertile pollen parent is also female fertile resulting in the production of inbred seed in addition to the hybrid seed produced on the seed parent. In most production methods this is solved by planting and harvesting the pollen parent and seed parent in physically separated strips or rows. However, hybrid seed yield in such a strip planting method is markedly lower compared to hybrid seed yield in a mixed planting of pollen parent and seed parent. With a field design where seed and pollen parent are planted in a mixed inter-planting fashion a mixture of hybrid and inbred seed is obtained. With techniques known today, a separation of the two different kinds of seed in order to obtain hybrid seed with a purity of greater than 90% is cumbersome. The use of biotechnologically introduced phenotypic markers (e.g. fluorescent seed color) enabling for seed separation without resulting in a phenotype visible to the grower or consumer is not generally accepted. Therefore, there is the need of new methods of separating hybrid seeds from inbred seeds based on natural traits. This problem is addressed by the present invention.

FIGURE LEGENDS

FIG. 1: Kernel phenotypes in cereals. Upper panel (wheat and oats): Free threshing seed with a softened, easily separable hull (left) and non-free threshing seed with a tenacious, tightly enclosing hull (right). The free-threshing phenotype is maternally determined. Lower panel (barley): free-threshing (naked) (left) and nonfree threshing (covered) seed (right), where the absence or presence of a sticky substance exuded from the seed (as indicated by the arrows) is suspected to determine the free-threshing phenotype.

Figure 2:
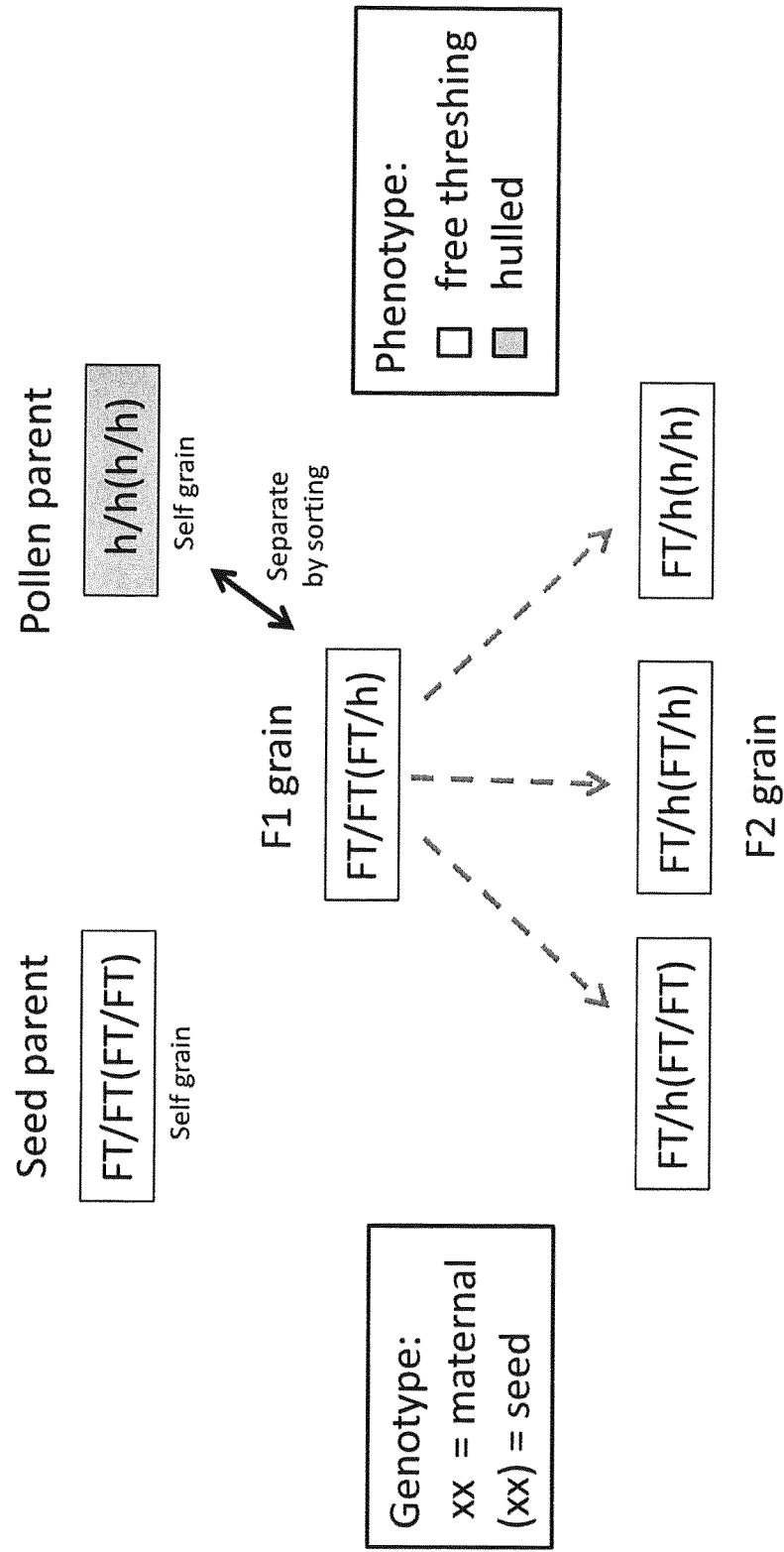

FIG. 2: Inheritance of threshability in cereals (wheat and oats) when seed parent is homozygous for one or more dominant free threshing (FT) allele(s) and the pollen parent is homozygous for one or more recessive hulled (h) allele(s), and the free-threshing phenotype is maternally expressed. The harvested seed from an F1 seed production field is a combination of free threshing hybrid seed from the seed parent and hulled inbred seed from the pollen parent, which can be separated by sorting, as indicated by the two-way arrow. The F2 grain resulting from planting of the hybrid seed is all free threshing.

Figure 3:
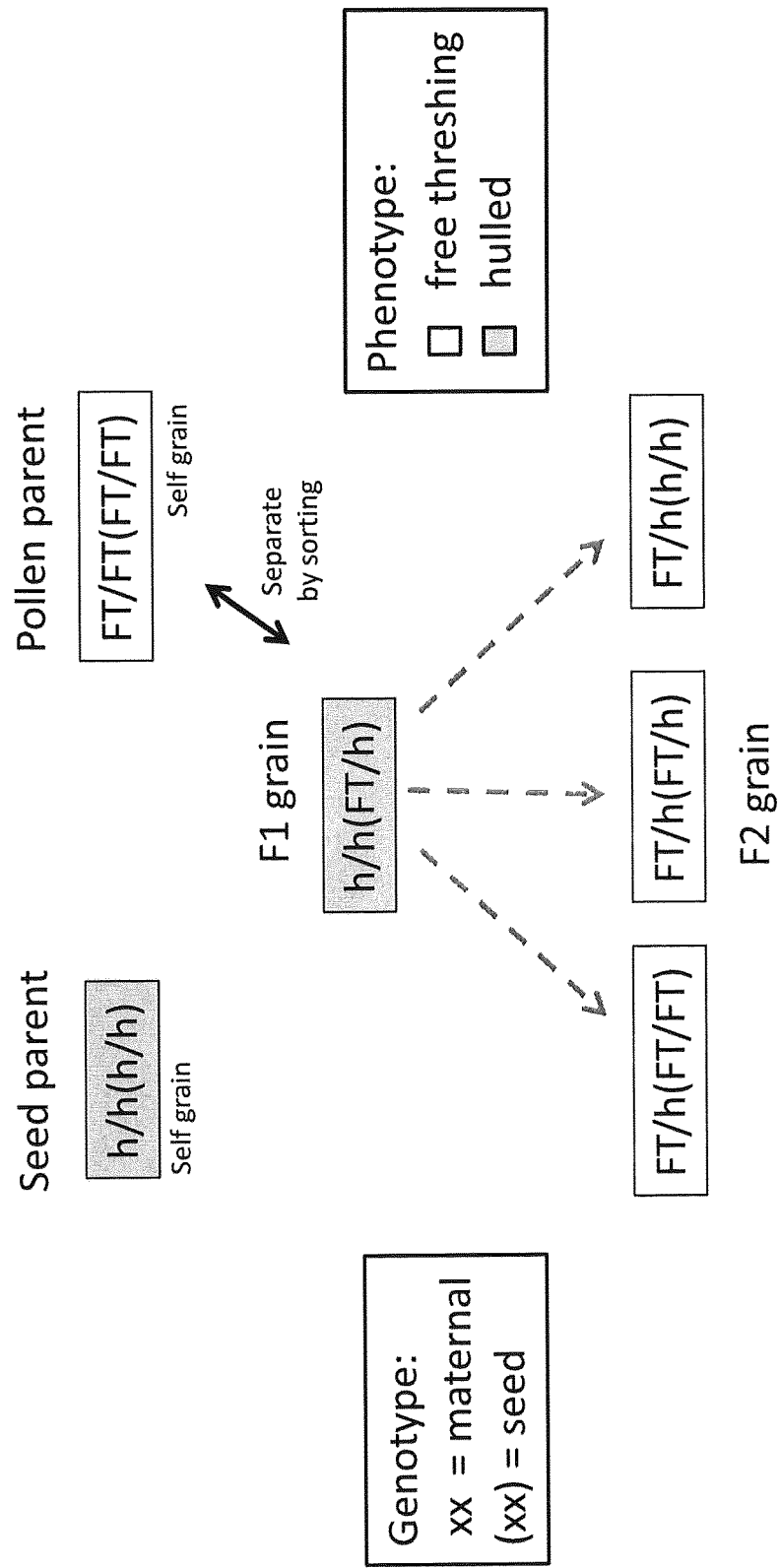

FIG. 3: Inheritance of threshability in cereals (wheat and oats) when seed parent is homozygous for one ore more recessive hulled (h) allele(s) and the pollen parent is homozygous for one or more dominant free threshing (FT) allele(s), and the free-threshing phenotype is maternally expressed. The harvested seed from an F1 seed production field is a combination of hulled hybrid seed from the seed parent and free threshing inbred seed from the pollen parent, which can be separated by sorting, as indicated by the two-way arrow. The F2 grain resulting from planting of the hybrid seed is all free threshing.

Figure 4:
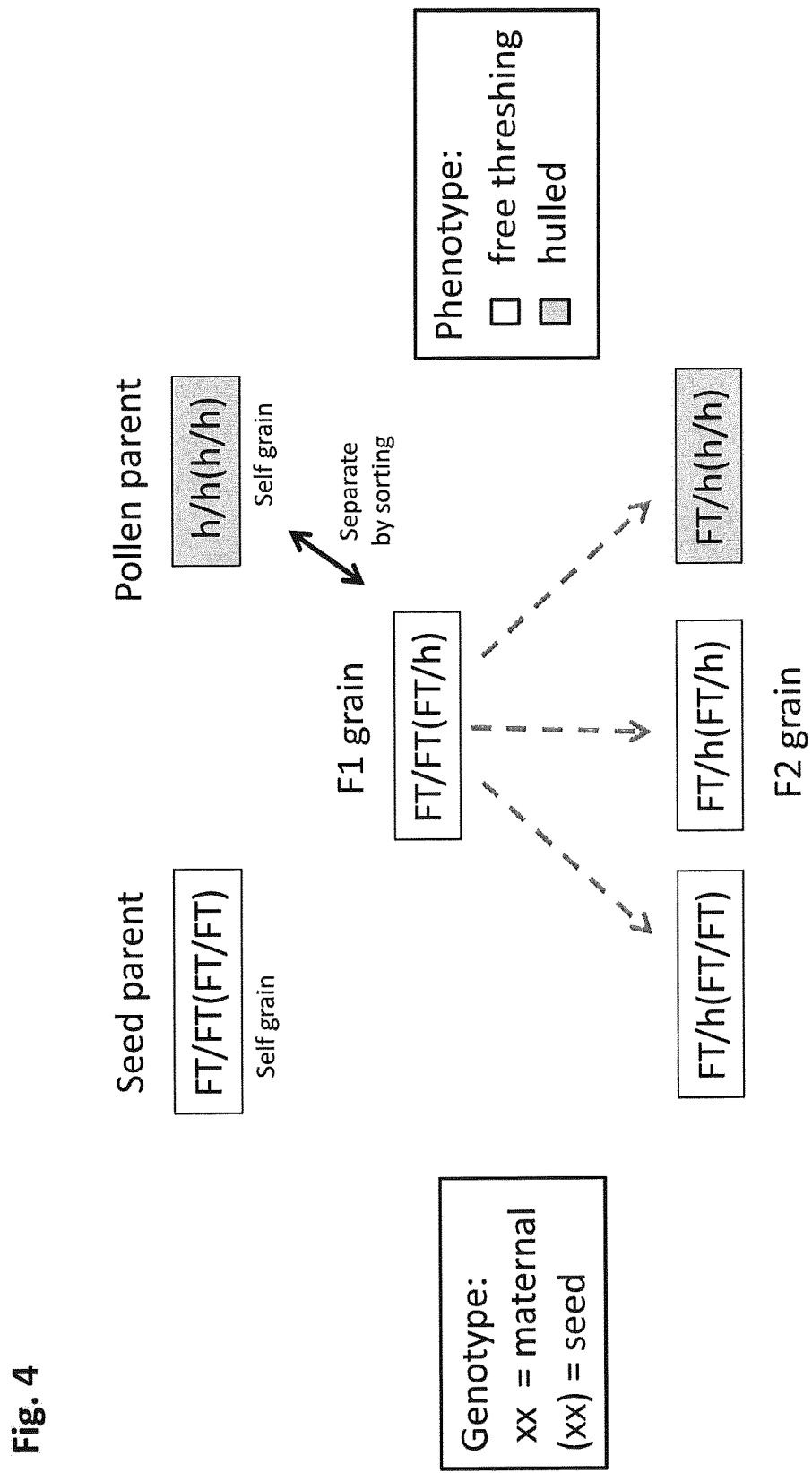

FIG. 4: Inheritance of threshability in cereals (wheat and oats) when the seed parent is homozygous for one or more dominant free threshing (FT) allele(s) and the pollen parent is homozygous for one or more recessive hulled (h) allele(s), and the free-threshing phenotype is expressed in the embryo or endosperm (principle). The harvested seed from an F1 seed production field is a combination of free threshing hybrid seed from the seed parent and hulled inbred seed from the pollen parent, which can be separated by sorting, as indicated by the two-way arrow. The F2 grain resulting from planting of the hybrid seed is a combination of free threshing and hulled seeds.

Figure 5:
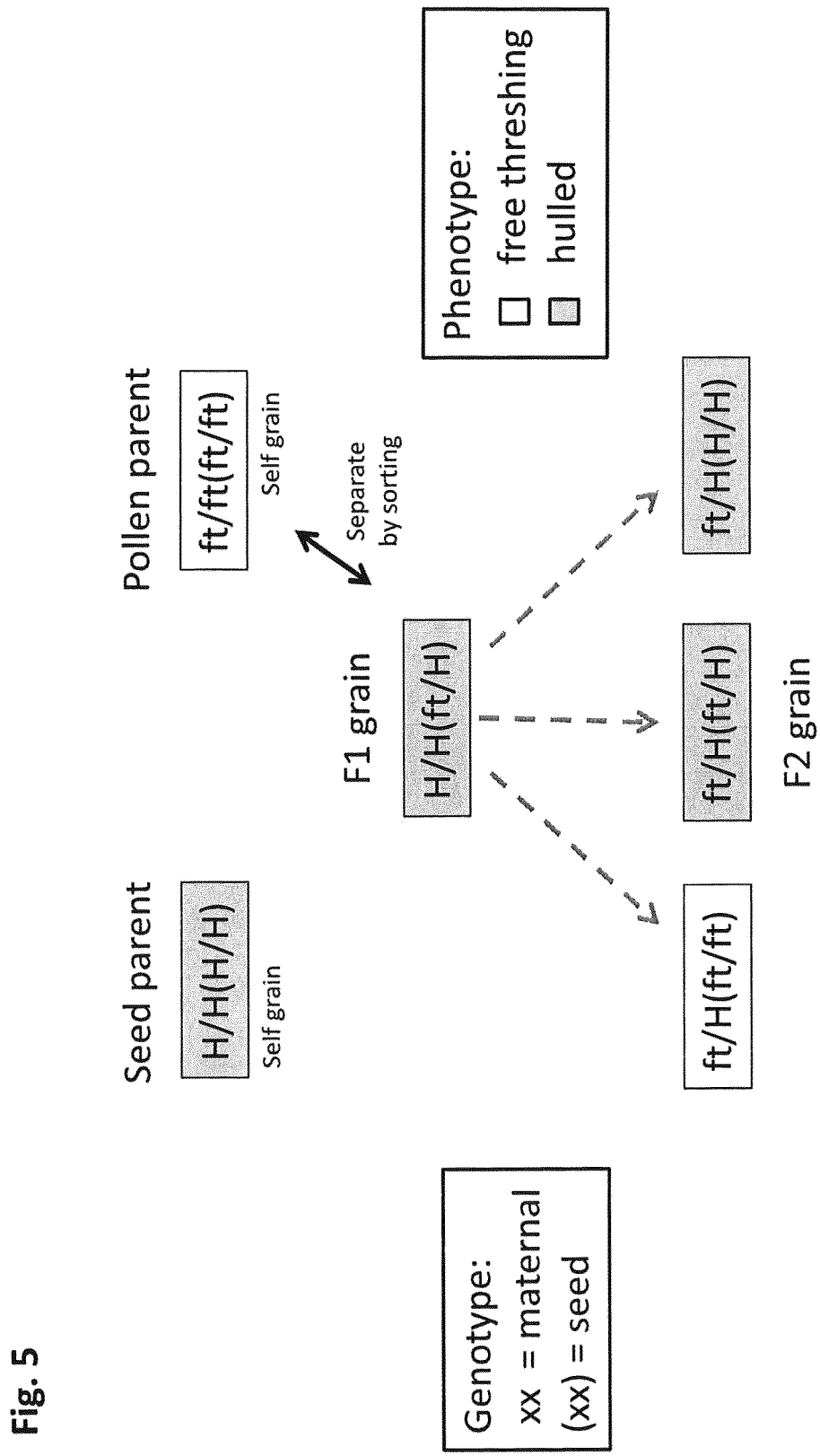

FIG. 5: Inheritance of threshability in cereals (barley) when the seed parent is homozygous for one or more dominant covered (H) allele(s) and the pollen parent is homozygous for one or more recessive naked (ft) allele(s), and the free-threshing phenotype is expressed in the embryo or endosperm. Harvested seed from an F1 seed production field is a combination of covered hybrid seed from the seed parent and naked inbred seed from the pollen parent, which can be separated by sorting, as indicated by the two-way arrow. The F2 grain resulting from planting of the hybrid seed is a combination of covered and naked seed.

Figure 6:
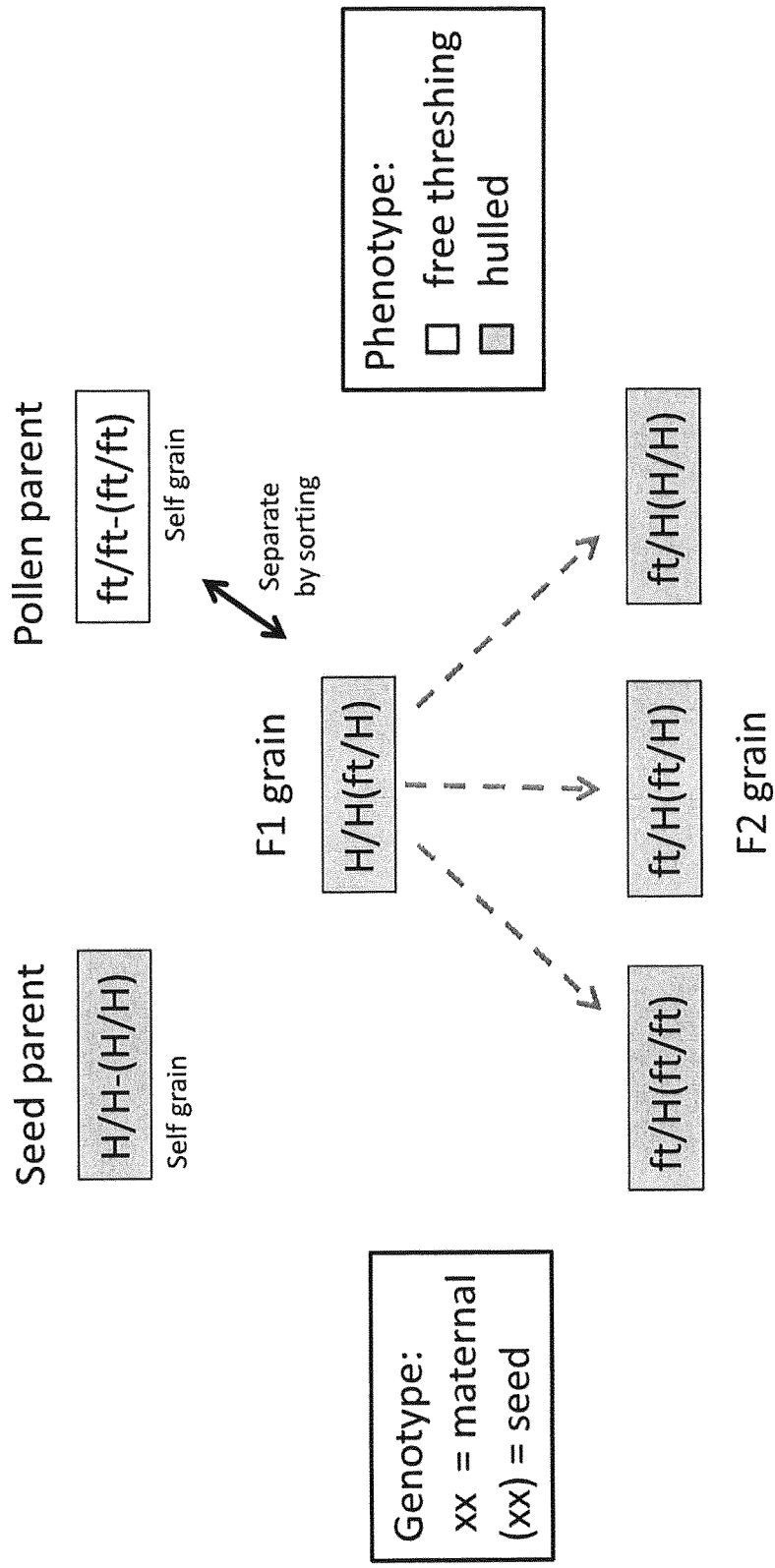

FIG. 6: Inheritance of threshability in cereals (barley) when the seed parent is homozygous for one or more dominant covered (H) allele(s) and the pollen parent is homozygous for one or more recessive naked (ft) allele(s), and the free-threshing phenotype is maternally expressed (principle). The harvested seed from an F1 seed production field is a combination of covered hybrid seed from the seed parent and naked inbred seed from the pollen parent, which can be separated by sorting, as indicated by the two-way arrow. The F2 grain resulting from planting of the hybrid seed is all covered.

FIG. 7: Inheritance of threshability in cereals (barley) when the seed parent is homozygous for one or more recessive naked (ft) allele(s) and the pollen parent is homozygous for one or more dominant covered (H) allele(s), and the free-threshing phenotype is maternally expressed (principle). The harvested seed from an F1 seed production field is a combination of covered hybrid seed from the seed parent and naked inbred seed from the pollen parent, which can be separated by sorting, as indicated by the two-way arrow. The F2 grain resulting from planting of the hybrid seed is all covered.

DETAILED DESCRIPTION

The present invention relates to a method of separating hybrid seeds of a cereal from a mixture comprising said hybrid seeds and inbred seeds of said cereal, comprising (a) obtaining or providing a mixture of seeds of a cereal obtained or produced by interplanting a combination of plants comprising a male sterile or conditionally male sterile seed parent and a male fertile pollen parent, wherein said seed parent and pollen parent produce at least two types of seeds, at least one of which being said hybrid seeds, said at least two types of seed having different phenotypes allowing separation of said hybrid seed with non-invasive methods based on the differences in said phenotypes, said different phenotypes being determined by an allele or a combination of alleles at one or more genetic loci, wherein said seed parent is homozygous for a first allele or combination of alleles at said one or more genetic loci resulting in a first phenotype and said pollen parent is homozygous for a second allele or combination of alleles at said one or more genetic loci resulting in a second phenotype; (b) separating said hybrid seeds using a separation method based on differences in said phenotypes.

Hybrid seeds are generally produced by cross-pollinated plants. In a more particular sense, the term refers to the seed resulting from specific and controlled crossing of two inbred lines. The embryo of said hybrid seed comprises one haploid genome copy of each parent. On the other hand, inbred seed is produced when the egg inside the ovary of a plant is fertilized by pollen originating from anthers borne in the same flower (in cereals called spikelets) as the ovary, anthers from other flowers of the same plant or anthers from the flowers of another plant of the same parental origin.

The term "cereal" relates to members of the monocotyledonous family Poaceae which are cultivated for the edible components of their grain. These grains are composed of endosperm, germ and bran. Maize, wheat and rice together account for more than 80% of the worldwide grain production. Other members of the cereal family comprise rye, oats, barley, triticale, sorghum, wild rice, spelt, einkorn, emmer, *durum* wheat and kamut.

Upon producing hybrid seed, a mixture of hybrid and inbred seed is obtained if the pollen parent is female fertile. Accordingly, a mixture of seeds comprising hybrid seeds can be obtained by interplanting a seed parent and a pollen parent. Possible scenarios of interplanting comprise strip or row planting where pollen and seed parent are planted in alternate rows. A more desirable type of interplanting comprises mixed interplanting, where a true mixture of pollen and seed parent is sown so that the pollen parent which is sown as a lower proportion than the seed parent is distributed evenly among the male sterile seed parent so that optimal cross-pollination can occur. This design is only feasible if the male sterile trait is inherent to the seed parent or can be induced due to a specific property of the seed parent.

Male sterile in connection with the present invention refers to the failure of plants to produce functional anthers, pollen or male gametes. This can be due to natural or artificially introduced genetic predispositions or to human intervention on the plant in the field.

Male fertile on the other hand relates to plants being capable of producing normal functional anthers, pollen and/or male gametes.

A pollen parent, is a parent plant that provides the male gametes (pollen) for fertilization, while a seed parent is the plant that provides the female gametes for fertilization, resulting in that plant bearing the seeds.

Both seed and pollen parent should be planted so that they flower at the same time, i.e. pollen of the pollen parent and the ovules of the seed parent are ripe at the same time. If there are differences in flowering times, planting times are to be adapted accordingly.

A seed parent can be male sterile and hence incapable of self-fertilization. A male-sterile seed parent can thus only produce seed when fertilized by pollen from a male fertile plant, i.e. the pollen parent. Vice versa, a pollen parent can be female sterile, thereby being incapable of self-fertilization. A female sterile pollen parent is thus only capable of fertilizing another female fertile plant, i.e. the seed parent. Reliably male sterile seed parents can be created in many crops. However, pollen parents in crops with "perfect" (bisexual) flowers, i.e. flowers comprising male and female organs are usually also female fertile and can therefore self-fertilize. In the present invention, the desired hybrid seed grows on the seed parent, whereas undesired contaminating inbred seed grows on the pollen parent.

At least two types of seeds, as used herein, relates to different parental origin and hence genetic constitution (which may translate into differences in phenotype) of the seeds resulting from (cross-)fertilization of types of genetically equal or different parent plants. For example, when both parents are fertile, the following types of seeds can be produced; seeds resulting from self-fertilization of the first parent, seeds resulting from self-fertilization of the second parent and seeds resulting from cross-fertilization (i.e. hybrid seed) borne by either the first or the second parent. In case of one parent being male sterile (i.e. the seed parent) and the other parent being completely fertile (the pollen parent), two types of seeds can arise, i.e. seeds resulting from cross-fertilization (i.e. hybrid seed) borne by the male sterile seed parent and seeds resulting from self-fertilization of the pollen parent. In case of a male sterile seed parent and female sterile pollen parent only one type of seed can arise, the hybrid seed.

Hybrid seed, as used herein, refers to seed resulting from a cross-fertilization of two parent plants that are not genetically identical, thus leading to seeds originating from the cross-fertilization having a different genetic constitution than either of the two parents.

Different phenotypes allowing separation of hybrid seed with non-invasive methods based on the differences in said phenotypes relates to methods that do not require removing parts of the seed or damaging the seeds in any way to establish said phenotypic differences, thereby ensuring that the seeds, upon planting, germinate and develop normally. Such methods include separation based on relative size of the seeds by sieving, separation based on specific weight by gravity sorting on a table sorter, separation based on specific weight by wind sieving, separation based on differences in color using non-invasive imaging techniques. Such methods are for example described in Dessai et al. (1997, Seeds handbook: biology, production, processing, and storage. Marcel Dekker, Inc., New York.), Harmond et al. (1968, Mechanical seed cleaning and handling. USDA Agricultural Handbook No. 354. Washington, D.C.), Jorgensen et al. (2004, Seed collection, cleaning, and storage, Chap. 24. In: Monsen et al. Restoring Western Ranges and Wildlands. USDA Forest Service Gen. Tech. Rep. RMRS-GTR-136. Ft. Collins, Colo.), Vaughan et al (1968, Seed processing and handling. Seed Technology Laboratory, Mississippi State Univ., State College, Miss., see also mcia.msstate.edu/pdf/seed-processing-and-handling.pdf) Emberson et al. (Optical sorting (2011): Grain, Feed and Milling technology, November-December 2011, p. 22-24), Delwiche et al. (2005, Applied Engineering in Agriculture, Vol. 21(4): 681-688), Dowell et al. (2002, Use of optical sorting to detect karnal bunt-infected wheat kernels. ASAE Paper No. 023007. St. Joseph, Mich.: ASAE. The methods of the invention may comprise more than one separation step, for example two sieving steps with different cut-offs (see also Example 3).

As used herein, the term "allele(s)" means any of one or more alternative forms of a gene at a particular locus. In a diploid cell of an organism, alleles of a given gene are located at a specific location or locus (plural: loci) on a chromosome. One allele is present on each chromosome of the pair of homologous chromosomes or possibly on homeologous chromosomes.

As used herein, the term "locus" (plural:loci) means a specific place or places or a site on a chromosome where for example a gene or genetic marker is found.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In tetraploid species, two sets of diploid genomes exist, whereby the chromosomes of the two genomes are referred to as "homeologous chromosomes" (and similarly, the loci or genes of the two genomes are referred to as homeologous loci or genes). Likewise, hexaploid species have three sets of diploid genomes, etc. A diploid, tetraploid or hexaploid plant species may comprise a large number of different alleles at a particular locus. The ploidy levels of domesticated wheat species range from diploid (*Triticum monococcum*, 2n=14, AA), tetraploid (*T. turgidum*, 2n=28, AABB) to hexaploid (*T. aestivum*, 2n=42, AABBDD).

As used herein, the term "heterozygous" means a genetic condition existing when two different alleles reside at a specific locus, but are positioned individually on corresponding pairs of homologous chromosomes in the cell. In other words, "heterozygous" means a genetic condition existing when two different alleles reside at a specific locus of the two members of a pair of homologous chromosomes in the cell. Conversely, as used herein, the term "homozygous" means a genetic condition existing when two identical alleles reside at a specific locus, but are positioned individually on corresponding pairs of homologous chromosomes in the cell. In other words, the term "homozygous" means a genetic condition existing when two identical alleles reside at a specific locus on both members of a pair of homologous chromosomes in the cell.

In the present invention, alternate alleles of one or more than one gene may determine the phenotype of the seed of inbred parent plants, whereby one allele or set of alleles determines one manifestation of the seed phenotype and another allele or set of alleles determines another manifestation of the seed phenotype and whereby one allele or set of alleles is dominant or partially dominant and the other allele or set of allelles is recessive or partially recessive. Accordingly, possible allele combinations specifying a particular seed phenotype include one dominant allele and one recessive allele as well as two dominant alleles, two recessive alleles, three dominant alleles, three recessive alleles, two dominant and one recessive allele, one dominant and two recessive alleles and all possible iterations for four, five, six or more genes involved in a specific phenotype according to the present invention. The same holds true for partially dominant and partially recessive alleles.

In another embodiment, the present invention relates to a method of producing hybrid seeds of a cereal comprising (a) interplanting a combination of plants comprising a male sterile or conditionally male sterile seed parent and a male fertile pollen parent, wherein said seed parent and pollen parent produce at least two types of seeds, at least one of which being said hybrid seeds, said at least two types of seed having different phenotypes allowing separation of said hybrid seed with non-invasive methods based on the differences in said phenotypes, said different phenotypes being determined by an allele or a combination of alleles at one or more genetic loci, wherein said seed parent is homozygous for a first allele or combination of alleles at said one or more genetic loci resulting in a first phenotype and said pollen parent is homozygous for a second allele or combination of alleles at said one or more genetic loci resulting in a second phenotype.

In a preferred embodiment, said method of producing hybrid seeds of a cereal further comprises separating the hybrid seeds using a non-invasive separation method.

In a preferred embodiment, said planting comprises row or strip planting or mixed interplanting.

In another preferred embodiment, said planting comprises sowing the seed of or planting young plants of said seed parent and said pollen parent into the soil.

In a further preferred embodiment, said method of producing hybrid seeds of a cereal further comprises harvesting the seeds produced prior to separating.

Harvesting may be effected, inter alia, by harvesting machines common in the art. In case of row or strip planting, harvesting machines are preferably designed so that the rows or strips of pollen plant can be harvested separately thus enabling for a pre-sorting of the resulting seeds.

In a preferred embodiment, said seed parent is homozygous for one or a combination of alleles at one or more genetic loci, wherein at least one of said alleles in said seed parent is dominant or partially dominant, and said pollen parent is homozygous for one or a combination of alleles at one or more genetic loci, wherein at least one of said alleles in said pollen parent is recessive or partially recessive.

The term "partial dominance" refers to the situation where the heterozygote displays a phenotype that is an intermediate between the phenotypes of both homozygote parent plants (one of which is homozygous (partially) dominant and the other is homozygous recessive). This intermediate phenotype is a demonstration of partial or incomplete dominance. When partial dominance occurs, a range of phenotypes is usually observed among the offspring. The same applies to partially recessive alleles. As used here, these terms imply that all alleles responsible for expression of hulled or free-threshing traits as explained further below, even if partially dominant or partially recessive, result in the expression of the desired phenotype, i.e. hulled or free-threshing seed.

The above combination of the genetic constitutions of the parents results in two types of seed being generated, wherein said two types of seed can be separated based on phenotype, as described above. When the seed parent is homozygous for one or more dominant alleles, the resulting hybrid seed also carries the maternal (dominant) phenotype; either because the phenotype of the seed is directly determined by genotype of the plant bearing the seeds (in this case the seed parent), as will be explained further below, or because of the genotype of the seed itself determining the seed phenotype. The inbred seed resulting from self-fertilization of the homozygous recessive pollen parent carries the (recessive) paternal phenotype, either because the phenotype of the seed is directly determined by genotype of the plant bearing the seeds (in this case the pollen parent), or because of the genotype of the seed itself determining the seed phenotype. This difference in the genotype of the plant bearing the seeds determining the seed phenotype vs. the genotype of the seed itself determining the seed phenotype is referred to as maternal expression vs. endosperm/embryonic expression.

In a more preferred embodiment, said combination of plants is characterized in that said one allele or combination of alleles at one or more genetic loci in said seed parent manifests in seeds with a free-threshing phenotype and wherein said one allele or combination of alleles at one or more genetic loci in said pollen parent manifests in seeds with a hulled phenotype.

Angiosperm seeds consist of three genetically distinct constituents: (1) the embryo formed from the zygote, (2) the endosperm, which is normally triploid, (3) the seed coat from tissue derived from the maternal tissue of the ovule. The seed coat is also referred to as husk or hull. The four wild species of wheat, along with the domesticated varieties einkorn, emmer and spelt, have hulls. This in evolutionary terms more primitive morphology which is also characteristic for barley consists of toughened or tenacious glumes that tightly enclose the grains, and, in domesticated wheats, a rachis that breaks easily on threshing. The result is that when threshed, the wheat ear breaks up into spikelets (also known as "speltoid phenotype"). To obtain the grain of hulled seed, further processing, such as milling or pounding, is needed to remove the hulls or husks. Hulled wheat seeds are often stored as spikelets because the toughened glumes give good protection against pests of stored grain. In contrast, in free-threshing (or naked) forms such as *durum* wheat and common wheat, the glumes are fragile and the rachis tough. On threshing, the chaff breaks up, releasing the grains.

Accordingly, in one embodiment, the seed parent is homozygous for a dominant or partially dominant allele or a combination of such alleles conferring the free-threshing phenotype, while the pollen parent is homozygous for a recessive allele or a combination of such alleles conferring the hulled phenotype. As a result, the hybrid seed will also be free-threshing whereas the selfed (inbred) seed is non-free-threshing (hulled).

In hexaploid wheat, the glume tenacity gene Tg along with the major domestication locus Q control threshability. The Q gene is a gene located on the long arm of wheat chromosome 5A (the Q locus) that is largely responsible for the domestication of wheat, as it confers the free threshing character by suppressing the speltoid phenotype. In addition, several positive pleiotropic effects are linked to Q, for example softening of the glumes, reduction of ear length, more spikelets per ear and toughness of the rachis, all of those features being favorable to harvesting (Salamini et al., 2002, Nature Reviews Genetics 3:429-441). The Q gene was cloned and molecularly characterized as an APETALA2 (AP2) like transcription factor. Of the two alleles, the Q allele appeared to be more abundantly transcribed than q, and can be differentiated by an A/G SNP at position 2123 of the Q gene, leading to a single amino acid difference between the Q and q protein. Accordingly, the Q protein is characterized by an isoleucine at position 329, while q has a valine at this position, the latter amino acid appearing to limit homodimer formation. The effect of Q mainly depends on its dosage. Based on dosage experiments of Q and q alleles in various backgrounds it was established that q is hypomorphic to Q and 2.5 doses of q equaled 1 dose of Q. In plants transformed with the Q allele, Q transcript levels were found to inversely correlate with the speltoid phenotype (Simons et al. 2006, Genetics 172: 547-555). Recently, a fast and reliable pyrosequencing application was developed to differentiate 5Aq and 5AQ alleles and determine 5AQ gene copy numbers in a single assay (Foerster et al., 2012, Euphytica 186:207-218).

Further determinant of the free threshing phenotype are the tenacious glume (Tg) gene and the soft glume (Sog) gene, that have been mapped to chromosomes 2DS and 2AS respectively, although the genes involved have not been identified yet. The Tg gene is a main threshability gene in hexaploid wheat, of which the Tg allele is partially dominant, while the free-threshing character of tg is recessive in nature. Sog is the main threshability gene in diploid wheat, the mutant allele (sog) being a recessive allele that confers a free threshing phenotype (Sood et al., 2009, Theor Appl Genet 199:341-351). Although in sog mutant plants the glumes that encase the grain are soft, the ears are very compact, which is a negative pleiotropic effect (Salamini et al., 2002, Nature Reviews Genetics 3:429-441)

Simonetti et al (1999, Genet Res Crop Evol 46:267-271) found in tetraploid wheat four QTLs influencing the threshability trait, associated with chromosomes 2BS, 5AL, 5AS, and 6AS. The 2BS and 5AL QTL corresponded to the homoeologous genes Tg and Q of hexaploid wheats, respectively, where Tg2 the putative ortholog of Tg, was located on chromosome 2BS (hereinafter referred to as $Tg^{2B}$, $Q^{5A}$ and $Tg^{2B}$). Thus, the fact that QTLs affecting the threshability of wheat have been identified on chromosome 6A and 6D (Simonetti et al., supra; Jantasuriyarat et al. 2004, Theor Appl Genet 108:261-273), suggests that loci other than those on group-2 chromosomes and chromosome 5A (Q gene) also may be involved in controlling the threshability trait in wheat (Sood et al., 2009, supra).

For example, free-threshing *durum* wheat thus can have the genotype $tgtg^{2B}QQ^{5A}$, while free-threshing bread wheat can have the genotype $tgtg^{2B}tgtg^{2D}QQ^{5A}$.

Accordingly, hulled *durum* wheat can have the genotype $tgtg^{2B}qq^{5A}$, while hulled bread wheat can have the genotype $tgtg^{2B}tgt^{2D}qq^{5A}$.

In oats (*Avena sativa*), kernel nakedness is a genetically complex trait; alleles at four different loci (designated as N-1, N-2, N-3 and N-4) are known to act epistatically to govern its expression. N-1 is the major switch gene conditioning nakedness, and alleles of the other three loci interact with N-1 and among each other to modify the degree to which nakedness is expressed. Depending on the alleles present at each the four loci, oat genotypes demonstrate different degrees of nakedness ranging from completely naked (or nearly naked) to partially naked, to partially covered, and all the way to completely covered phenotypes. A completely naked phenotype is expressed when dominant alleles are present at the N-1 and N-2 loci, and either the dominant (N-3) or the recessive (n-3) allele is present at the third locus. Genotypes with homozygous recessive (n-1/n-1) alleles at the N-1 locus will always have the covered phenotype regardless of the alleles present at the other loci. N-1/N-1 genotypes may have either naked or mosaic phenotypes depending on the alleles present at the other loci. The mosaic phenotype produces a mixture of naked and covered kernels, of various proportions, depending on the alleles present at the N-2 and N-3 loci. The N-4 locus reverses the effects of the other three loci. In a homozygous recessive (n-4/n-4) condition it is hypostatic to any dominant allele at the other three loci. When the N-4 locus is homozygous dominant (N-4/N-4) and the N-1 locus is in a heterozygous condition, a covered phenotype is produced. An esterase isozyme marker was found to be tightly linked to one of the genes (presumably N-1) conditioning nakedness in oats (Kibite 2002, An Isozyme Marker linked to the N-1 Gene Governing Nakedness in Oat, in: Oat newsletter Vol48).

For example, according to the knowledge available so far, free-threshing oats thus can have the genotype N-1/N-1 together with N-2/N-2 and N-3/N-3 or together with N-2/N-2 and N-3/n-3 and n-4/n-4, while hulled oats can have the genotype n-1/n-1 and N-4/N-4 or N-1/n-1 and N-4/N-4, where the status of N-2 or N-3 is irrelevant.

In most cereals, including wheat and oats, the seed phenotype in terms of hulls is maternally determined as the seed coat is in fact maternal tissue. This means that the genotype of the parent plant bearing the seeds determines whether the seed borne by that plant (i.e. the F1 seed) is either hulled of free-threshing. Consequently, the genotype of the F1 seed parent determines the phenotype of the seed born by that plant, i.e. of the F2 seed, etc. In connection to the present invention, the threshability phenotype of hybrid seed borne by the seed parent is determined by the genotype of the seed parent, while seed borne by the pollen parent as a result of self-fertilization of thus has the phenotype as determined by the genotype of the pollen parent. This principle of the genotype of plant bearing the seed directly determining the seed phenotype is referred to as maternal expression of the seed phenotype.

In a more preferred embodiment, said combination of plants is characterized in that said one allele or combination of alleles at one or more genetic loci in said seed parent manifests in seed with a hulled phenotype and wherein said one allele or combination of alleles at one or more genetic loci in said pollen parent manifests in seeds with a free-threshing phenotype.

Barley is an exception to the above principle of the maternal expression of the seed threshability phenotype. In contrast to other cereals such as wheat and oats, barley typically has caryopses with adhering hulls at maturity, known as covered (hulled) barley. A few barley cultivars however are a free-threshing, also called naked (hull-less) barley. In covered barley, a sticky adhesive substance appears 10 days after flowering on the caryopsis surface and that the substance is produced by the caryopsis (i.e. by the embryo/endosperm), not by the hull (maternal tissue). The covered/naked caryopsis in barley is controlled by a single locus (nud, for nudum) located on chromosome arm 7HL; the covered caryopsis allele (Nud) being dominant over the naked one (nud). The Nud gene was identified as an ethylene response factor (ERF) family transcription factor gene. A 17-kb deletion harboring the ERF gene was found among 100 naked cultivars studied, while two X-ray induced nud alleles containing non-synonymous amino acid substitutions further confirmed the ERF gene to be responsible for the covered/naked seed phenotype in barley. By analogy to the deduced functions of the related *Arabidopsis* WIN1/SHN1 gene, it is believed the barley Nud gene regulates composition of lipids deposited on the pericarp epidermis, thereby controlling adhesion of the hull, while in naked barley, the lack of the lipid layer probably blocks adhesion, thereby rendering free-threshing caryopses (Taketa et al., 2008, PNAS 11: 4062-4067).

Accordingly, in barley the naked/hulled phenotype of the seed is determined by the Nud genotype of the seed itself (i.e. embryo/endosperm determined) and not by the genotype of the seed parent (not maternally determined). This is referred to as endosperm/embryonic expression of the seed phenotype. As a consequence, hulled barley has a genotype of Nud/Nud or Nud/nud, whereas naked barley has a genotype of nud/nud.

In a preferred embodiment, said seed parent is homozygous for one or a combination of alleles at one or more genetic loci, wherein at least one of said alleles is recessive or partially recessive, and said pollen parent is homozygous for one or a combination of alleles at one or more genetic loci, wherein at least one of said alleles is dominant or partially dominant. In this embodiment, the seed phenotype should be maternally expressed.

In another preferred embodiment, said combination of plants is characterized in that said one allele or combination of alleles at one or more genetic loci in said seed parent manifests in seeds with a hulled phenotype and said one allele or combination of alleles at one or more genetic loci in said pollen parent manifests in seeds with a free-threshing phenotype.

An overview of the genetic determinants and inheritance of hulled vs. free threshing phenotype in various cereals is given below in table 1 and is schematically depicted in FIGS. 1-7.

TABLE 1

Constitution of the parental and F1 grain and inheritance (simplified)

| Cereal species | Phenotype of seed parent | Phenotype of pollen parent | Target fraction Phenotype of harvested F1 (hybrid) seed | Phenotype of F2 seed | Inheritance and expression of the free threshing type |
|---|---|---|---|---|---|
| Barley | Hulled | Free threshing | Hulled | Hulled | Recessive; endosperm/embryo |
| Oats | Free threshing | Hulled | Free treshing | Free treshing | Dominant (partial); maternal |
| Wheat | Free threshing | Hulled + nonbrittle | Free threshing | Free threshing | Dominant for Q-factor/recessive for all others (tg, sog,); maternal |

Said non-invasive separation method can be based on differences in size, surface condition or specific weight of said at least two types of seed as described above.

For embodiments where the difference in phenotypes is expressed via a hulled and free-threshing phenotype, separation can be effected based on different sizes of the grains with and without hulls. Whereas the grains themselves usually have the same or a comparable size, the presence of the hulls tightly attached to the grains of one phenotype makes the volume of this type of seed larger than that of the free-threshing grains alone. An alternative separation method may be based on specific weight of the seed. Hulled seed, due to its bigger volume which is partly filled only by air, has a lower specific weight than free-threshing seed.

The present invention also relates to a method of separating hybrid seed from a mixture of hybrid seed and inbred seed comprising obtaining or providing said mixture, wherein embryos of said hybrid seeds have a genotype comprising one haploid genome copy of the seed parent and one haploid genome copy of the pollen parent, wherein embryos of said inbred seeds have a genotype comprising two haploid genome copies of the pollen parent, wherein said seed parent is male sterile or conditionally male sterile and wherein said pollen parent is male fertile, characterized in that (a) said seed parent is homozygous for seed with a free-threshing phenotype and said pollen parent is homozygous for seed with a hulled phenotype, or (b) said seed parent is homozygous for seed with a hulled phenotype and said pollen parent is homozygous for seed with a free-threshing phenotype; comprising applying said mixture of seeds to a means for separation according to size, surface condition or specific weight of the grains.

In a preferred embodiment, the ratio of pollen parent to seed parent is 1:100 to 25:100.

Depending on the type of interplanting, different ratios of pollen parent to seed parent may be necessary. For the case of row or strip planting, the ratio of pollen parent to seed parent may be ranging from 10:100 to 25:100, such as 15:100 or 20:100. For mixed interplanting, less pollen parent is needed to ensure fertilization of the seed parent. Commonly used ratios range between 1:100 and 15:100, such as 2:100, 3:100, 5:100, 8:100, 10:100 or 12:100.

Said cereal may be selected from wheat, *durum*, oat, barley and triticale.

In a more preferred embodiment, said cereal is wheat and said seed parent is selected from *Triticum aestivum* L. ssp. *Vulgare* Host, *Triticum aestivum* L. ssp. *Compactum*, *Triticum aestivum* L. ssp. *Sphaerococcum*, *Triticum aestivum* L. ssp. *Petropavlovskyi* and *Triticum aestivum* L. ssp. *Tibetianum*.

In another more preferred embodiment, said cereal is wheat and said pollen parent is selected from *Triticum aestivum* L. ssp. *Spelta*, *Triticum aestivum* L. ssp. *Macha*, *Triticum aestivum* L. ssp. *Vavilovii*, *Triticum aestivum* L. ssp. *Yunnanense* and a semi-wild form of *Triticum aestivum* L. ssp. *Tibetianum*.

In a more preferred embodiment, the cereal is wheat and seed parent and pollen parent are combined from the above listed cultivars.

In a preferred embodiment, said cereal is *durum* wheat and said seed parent is selected from *T. turgidum* L. ssp. *Durum Desf.* and *T. turgidum* L. ssp. *Parvicoccum*. In another preferred embodiment, said cereal is *durum* wheat and said pollen parent is selected from *T. turgidum* L. ssp. *Dicoccum* (emmer) and *T. turgidum* L. ssp. *Dicoccoides* (wild emmer). In a more preferred embodiment, the cereal is *durum* wheat and seed parent and pollen parent are combined from the above listed cultivars.

In another preferred embodiment, the genes determining said hulled phenotype are recessively inherited.

In a further preferred embodiment, said male sterility is based on cytoplasmic male sterility, nuclear male sterility or a trait introduced into said plant by genetic engineering or mutation, or induced using a gametocide.

During wheat hybrid seed production, different methods can be used to prevent self-pollination of the female line: application of male-specific gametocides on the seed parent, use of genetic cytoplasmic or nuclear-encoded male sterility or use of a trait introduced into the plant by genetic engineering or mutation (for a review see also Perez-Prat and van Lookeren Campagne, 2002, Trends Plant Science 7(5), 199-203, herewith incorporated into the present application in its entirety).

Cytoplasmic male-sterile (CMS) lines have one or more mutations in their mitochondrial genome (termed "sterile cytoplasm") resulting in male sterility, and the male sterility is inherited as a dominant, maternally transmitted trait. For cytoplasmic male sterility to be used in hybrid seed production, the seed parent must contain a sterile cytoplasm and the pollen parent must contain (nuclear) restorer genes to restore the fertility of the hybrid plants grown from the hybrid seed harvested from the seed parent; and the CMS mutation should not be associated with a yield penalty.

Biotechnology has added new possibilities to obtain male-sterile plants, i.e. by introducing genes resulting in traits that confer (conditional) male sterility. For example, a gene, or set of genes may be introduced via genetic engineering, said genes being able to alter the levels of metabolites needed for the production of viable pollen, such as amino acids (WO94/29465), sugars (Goetz et al., 2001, PNAS 98, 6522-6527), flavonols (Derksen et al., 1999, Planta 207, 575-581), jasmonic acid (WO97/10703, McConn and Browse, Plant Cell 8, 403-416; Sanders et al., Plant Cell 12, 1041-1061), biotin (WO99/04023) or auxins (Spena et al., 1992, Theor. Appl. Genet. 84, 520-527). Inducible fertility can be achieved for some of these systems by application of the missing metabolite (see e.g. WO97/10703, McConn and Browse, Plant Cell 8, 403-416; Sanders et al., Plant Cell 12, 1041-1061, WO99/04023, WO93/18142, EP0513884).

Another approach to general male sterility is effected by the combined action of two (trans)genes brought together into the same plant by crossing two different parental lines each expressing one of the genes (see. E.g. U.S. Pat. No. 5,426,041 or WO98/32325). An example of this approach is the reconstitution of an active toxin from two inactive toxin fragments each encoded by a separate transgene. The combined expression of both transgenes in the male reproductive tissues can result in male sterility. This strategy requires a pollination control system to cross the two fertile grandparent lines to produce the male-sterile female parent line for hybrid seed production.

Systems that rely on the selective removal of tissues needed for the production of functional pollen by the tissue-specific expression of a gene encoding a protein able to disrupt cell function can be based on both natural traits and genetically engineered traits (see. e.g. Mariani et al., 1990, Nature 347, 737-741; Koltunow et al, 1990, Plant Cell 2, 1201-1224; U.S. Pat. Nos. 6,072,102 and 5,880,333). Some of these offer the possibility for chemical control of sterility or of fertility. For example, inducible sterility can be obtained by expressing a gene encoding a protein that catalyzes the conversion of a pro-herbicide into a herbicide only in male reproductive tissues (see e.g. O'Keefe et al., 1994, Plant Physiol. 105, 473-482; Kriete et al., 1996, Plant J. 9, 809-818; Dotson et al., 1996, Plant J. 10, 383-392 and U.S. Pat. No. 6,177,616), or by engineering the male sterility gene in such a way that its expression can be induced by the application of a chemical. Similarly, chemical regulation of the expression of a gene that can complement the male sterility (fertility restorer gene) or of a repressor of the male sterility gene can be used to induce fertility (see e.g. U.S. Pat. No. 6,072,102; Ward et al., 1993, Plant Mol Biol 22, 361-366, WO99/42598; U.S. Pat. No. 6,172,279 and WO93/18171).

Finally, the possibility of making use of natural or induced mutations that cause male sterility has also been described. In this case, the wild-type allele is used as a fertility restorer gene, and its expression is controlled by the application of chemicals.

One of the most straightforward ways to propagate male-sterile plants is to link a gene conferring dominant male sterility to an herbicide tolerance gene. The heterozygous male-sterile plants are crossed with a wild-type line in the same (isogenic) genetic background. The male-sterile progeny of this cross is selected by herbicide application (see e.g. WO89/10396). This strategy is used successfully for the commercial production of canola hybrids (Brassica napus) in Canada.

The present invention also relates to hybrid cereal seed produced by the methods of the invention as described above.

Furthermore, the present invention relates to hybrid cereal seed, wherein embryos of said hybrid seeds have a genotype comprising one haploid genome copy of the seed parent and one haploid genome copy of the pollen parent, optionally wherein said seed parent is male sterile or conditionally male sterile, wherein said pollen parent is male fertile, characterized in that (a) said seed parent is homozygous for seed with a free-threshing phenotype and said pollen parent is homozygous for seed with a hulled phenotype; or b) said seed parent is homozygous for seed with a hulled phenotype and said pollen parent is homozygous for seeds with a free-threshing phenotype.

The present invention also relates to the use of (a) a male sterile or conditionally male sterile seed parent producing seeds with a free-threshing phenotype of a cereal and a pollen parent homozygous for seed with a hulled phenotype of said same cereal, or (b) a male sterile or conditionally male sterile seed parent of a cereal producing seed with a hulled phenotype and a pollen parent homozygous for seed with a free-threshing phenotype for producing hybrid seed of said cereal.

The present invention also relates to hybrid seed obtained by any of the methods described herein.

The examples illustrate the present invention.

Example 1: Separation of Artificial Seed Mixtures

Commercial hulled and free threshing varieties from three cereal species (table 2) were grown at two locations (D-78224 Bohlingen (BO), D-06466 Gatersleben (GA)) and harvested. Two locations where chosen in order to consider influence of environment on plant development and grain sizes. Harvested seed was cleaned from dirt and other unwanted material by wind sieving. The thousand kernel weight (TKW) of the different seed samples was determined (table 3). Seed mixtures were produced in order to have 85% of seed parent seeds and 15% of pollen parent seeds (table 3). Subsamples of 100 g of the mixtures were exposed to simple sieving, using a "Pfeuffer Sortimat" laboratory sieving machine equipped with different sieves of 2.8, 2.7, 2.6, 2.5, and 2.2 mm broadness respectively and 20 mm length. Sieving fractions were weighed and sorted by hand in order to determine the number of hulled and free threshing seeds respectively. Results are reported on the sieve which resulted in optimal purity of the target fraction after one sieving step.

TABLE 2

| | | | Sample varieties | |
|---|---|---|---|---|
| Entry | Sample no | Species | Seed parent Example variety | Pollen parent Example variety |
| 1 | 1 | Barley | Henrike (hulled) | Pastello (free threshing) |
| 2 | 2 | Barley | Westminster (hulled) | Pastello (free threshing) |
| 3 | 10 | Oats | Samuel (free threshing) | Scorpion (hulled) |
| 4 | 21 | Wheat | Tabasco (free threshing) | Badenstern (hulled) |
| 5 | 22 | Wheat | Genius (free threshing) | Badenkrone (hulled) |

TABLE 3

| | | mixing procedure (mixture in % by number of seeds) | | | | | | |
|---|---|---|---|---|---|---|---|---|
| | | | | TKW (g) | | Mixture % by number of | | Mixture weight (g) |
| Entry | Species | Mixture partners | Location | hulled | free threshing | hulled | free threshing | hulled | free threshing |
| 1 | Barley | Henrike-Pastello | BO | 55.5 | 40.5 | 85.0 | 15.0 | 472.0 | 61.0 |
| 1 | Barley | Henrike-Pastello | GA | 51.0 | 49.0 | 85.0 | 15.0 | 130.1 | 22.1 |
| 2 | Barley | Westminster-Pastello | BO | 53.5 | 40.0 | 85.0 | 15.0 | 455.0 | 60.0 |
| 2 | Barley | Westminster-Pastello | GA | 49.3 | 48.0 | 85.0 | 15.0 | 125.7 | 21.6 |
| 3 | Oats | Scorpion-Samuel | BO | 36.0 | 28.6 | 15.0 | 85.0 | 27.0 | 121.6 |
| 3 | Oats | Scorpion-Samuel | GA | 39.7 | 26.6 | 15.0 | 85.0 | 29.8 | 113.1 |
| 4 | Wheat | Badenstern-Tabasco | GA | 168.0 | 47.0 | 15.0 | 85.0 | 126.0 | 199.8 |
| 5 | Wheat | Badenkrone-Genius | GA | 160.6 | 47.6 | 15.0 | 85.0 | 120.5 | 202.3 |

Table 4 shows the target fractions after sieving a sample of 100 g. The number of hulled and free threshing seeds was counted in the target fraction. It was possible to enrich the target fraction in all species and environments higher than the required threshold of 90%. In barley the purity of the target fraction varied from 90% to 95%. The variation of the purity in oats varied between 94% and 96%. The best results for separating hulled and free threshing seeds could be found for wheat. The purity of the target fraction in wheat was in both entries Badenstern-Tabasco and Badenkrone-Genius more than 99%.

TABLE 4

Purity of the target fraction by separation of hulled and free threshing mixtures after one single sieving step. Sieving of 100 g of seed mixture.

| Entry | Species | Mixture Partners | Location | Sieve and fraction | Weight (g) | Number of seeds hulled | Number of seeds free threshing | % of purity of the target fraction after |
|---|---|---|---|---|---|---|---|---|
| 1 | Barley | Henrike Pastello | BO | 2.7 mm Oberfraktion | 89.2 | 1465 | 90 | 94.2% |
| 2 | Barley | Westminster-Pastello | BO | 2.7 mm Oberfraktion | 90.5 | 1568 | 133 | 92.2% |
| 3 | Oats | Scorpion-Samuel | BO | 2.6 mm Unterfraktion | 79.2 | 162 | 2663 | 94.3% |
| 1 | Barley | Henrike Pastello | GA | 2.6 mm Oberfraktion | 83.9 | 1482 | 111 | 93.0% |
| 2 | Barley | Westminster-Pastello | GA | 2.7 mm Oberfraktion | 69.3 | 1213 | 61 | 95.2 |
| 2 | Barley | Westminster-Pastello | GA | 2.6 mm Oberfraktion | 81.9 | 1408 | 155 | 90.1% |
| 3 | Oats | Scorpion Samuel | GA | 2.6 mm Unterfraktion | 79.7 | 116 | 2913 | 96.2% |
| 4 | Wheat | Badenstern-Tabasco | GA | 3.0 mm Unterfraktion | 61.4 | 2 | 1305 | 99.8% |
| 5 | Wheat | Badenkrone-Genius | GA | 3.0 mm Unterfraktion | 62.7 | 5 | 1313 | 99.6% |

Oberfraktion = target fraction in barley: seeds not gone through the sieve have been collected.
Unterfraktion = target fraction in wheat and oats: seeds gone through the sieve have been collected.

TABLE 5

Efficiency of sieving a mixture of hulled and free threshing seed sample in different species

| | | | | % of purity of the target fraction (number of seeds) | |
|---|---|---|---|---|---|
| Entry | Species | Mixture Partners | Location | Sieve and fraction | Before sieving | After sieving |
| 1 | Barley | Henrike Pastello | BO | 2.7 mm Oberfraktion | 85% | 94.2% |
| 2 | Barley | Westminster-Pastello | BO | 2.7 mm Oberfraktion | 85% | 92.2% |
| 3 | Oats | Scorpion Samuel | BO | 2.6 mm Unterfraktion | 85% | 94.3% |
| 1 | Barley | Henrike-Pastello | GA | 2.6 mm Oberfraktion | 85% | 93.0% |
| 2 | Barley | Westminster-Pastello | GA | 2.7 mm Oberfraktion | 85% | 95.2% |
| 2 | Barley | Westminster-Pastello | GA | 2.6 mm Oberfraktion | 85% | 90.1% |
| 3 | Oats | Scorpion Samuel | GA | 2.6 mm Unterfraktion | 85% | 96.2% |
| 4 | Wheat | Badenstern-Tabasco | GA | 3.0 mm Unterfraktion | 85% | 99.8% |
| 5 | Wheat | Badenkrone-Genius | GA | 3.0 mm Unterfraktion | 85% | 99.6% |

The hulled and free threshing seed show different colors. The difference in seed color would allow the seed processor to remove further pollen parent seeds by color sorting machines.

In conclusion, by combining simple sieving techniques with standard color sorting techniques it is possible to enrich the fraction of F1 seeds harvested from a mixed planting to more than 99%.

Example 2: Separation of Harvested Seed Mixtures from Strip Planting

Hulled and free threshing commercial wheat varieties (Table 6) were grown at the location D-78224 Bohlingen. The field design is shown in table 7. For an effective gametocide application, row planting is necessary. The seed parent row was flanked by rows of the pollen parent. As this was a small scale demonstration, rows of 1.0 m length were planted with a plant breeder's sowing machine. One plot therefore consisted of three rows.

TABLE 6

| parents | |
|---|---|
| Seed parent wheat (*Triticum aestivum*) free threshing | Pollen parent spelt wheat (*Triticum spelta*) hulled |
| Egoist | Badenstern |
| Meister | |
| Tobak | |

TABLE 7 field design

| Row number | 1 | 2 | 3 |
|---|---|---|---|
| Spacing (m) | 0.2 | 0.4 | 0.2 |
| Row length (m) | 1 | 1 | 1 |
| Treatment with Gametocide | no | yes | no |
| Species | Triticum spelta | Triticum aestivum | Triticum spelta |
| Parent | Pollen parent | Seed parent | Pollen parent |
| Combination 1 | Badenstern | Egoist | Badenstern |
| Combination 2 | Badenstern | Meister | Badenstern |
| Combination 3 | Badenstern | Tobak | Badenstern |

In due time, male sterility of the seed parent (middle row) was introduced via treatment with a gametocide (e.g. Genesis) according to the gametocide's instruction manual. Successful introduction of male sterility of the seed parent was checked by bagging some single ears within the seed parent row. Bagged single ears showed no seed set.

All three rows were harvested together. Harvested seed was cleaned from dirt and other unwanted material by wind sieving.

Subsamples of 80 g of the plot mixtures were exposed to simple sieving, using a "Pfeuffer Sortimat" laboratory sieving machine equipped with different sieves of 3.0, 2.8, 2.7, and 2.5 mm broadness respectively and 20 mm length. Sieving fractions were weighed and sorted by hand in order to determine the number of hulled and free threshing seeds respectively.

Due to the architecture of the hulled versus the free threshing wheat seed, separation was already successful with a 3.0 mm sieve after one sieving step, and a more that 99% purity of seed harvested from the seed parent could be achieved.

TABLE 8

Sieving of harvested F1 seed mixtures

| Combination | Seed parent | Pollen parent | Yield mixture of seed parent and pollen parent (g) | weight of pollen parent after sieving (3.0 mm sieve) (g) | weight of seed parent after sieving (3.0 mm sieve) (g) | Purity of seed parent after sieving (% number of seeds) |
|---|---|---|---|---|---|---|
| 1 | Egoist | Badenstern | 164 | 123 | 41 | 99.1 |
| 2 | Meister | Badenstern | 141 | 114 | 27 | 99.8 |
| 3 | Tobak | Badenstern | 180 | 136 | 44 | 99.4 |

Thus, by simple sieving techniques it is possible to enrich the fraction of F1 wheat seeds harvested in a mixture from row planting to more than 99%.

Example 3: Production of Wheat Hybrid Seed by Using Hulled Pollen Parents, where the Seed Parent Exhibits Cytoplasmatic Male Sterility (CMS) and is a Free Threshing Hexaploid Winter Wheat The pollen sterile A-line "CMS-WW005" (*Triticum aestivum*) was used as a seed parent. This line exhibits cytoplasmatic male sterility (CMS). This line is a free threshing hexaploid winter wheat. Hybrid production was performed in mixed planting in the greenhouse at Gatersleben. Seed parent was pollinated by open pollination with the pollen parents of the variety Badenstern or Badenkrone (*Triticum spelta*). Badenstern or Badenkrone are fully fertile pollen parents with non-free threshing (hulled) grain set. Another hybrid seed production was performed in mixed planting in the counter season nursery in Pochefstroom/Rep. South Africa. Mixing rate was 50% seed parent and 50% pollen parent in order to have enough pollen. Plot size at all locations was 1 m*1.2 m, with four rows in Gatersleben and three rows in Pochefstroom.

TABLE 1 parents

| Seed parent wheat (*Triticum aestivum*) free threshing | Pollen parent spelt wheat (*Triticum spelta*) hulled | Grown in Gatersleben (green house) | Grown in Pochefstroom |
|---|---|---|---|
| CMS-WW005 | Badenstern | Yes sample 1 | Yes sample 2 |
| CMS-WW005 | Badenkrone | no | Yes, but no F1 seeds produced sample 4 |
| — | Badenstern | Yes sample 3 | no |

In due time, male sterility of the seed parent was checked by bagging some single ears of seed parent plants. Bagged single ears showed no seed set.

At both locations, plots were harvested and threshed. Harvested seed was cleaned from dirt and other unwanted material by wind sieving. Seeds from the counter season nursery was sent to Gatersleben for further examination. Sample 4, i.e. the harvest from the production of CMS-WW005*Badenkrone at Pochefstroom, did not contain F1 seeds but only inbred seeds from the pollen parent, as the nicking was insufficient (flowering time of seed and pollen parent differed too much) and seed parent plants were not pollinated. Sample 3 only contained inbred seed from the pollen parent Badenstern and was harvested in Gatersleben for comparison purposes.

Subsamples of 80 g of the samples were exposed to simple sieving, using a "Pfeuffer Sortimat" laboratory sieving machine equipped with different sieves of 3.0, 2.8, 2.7, and 2.5 mm width respectively and 20 mm length. Sieving fractions were weighed and sorted by hand in order to determine the number of hulled and free threshing seeds respectively.

Due to the architecture of the hulled versus the free threshing seed, separation was very successful with a 3.0 mm sieve after one sieving step, and a fraction of more than 90% of free threshing seeds was obtained (Table 2). That fraction still contained broken husks of hulled seed, which were easily removed by a seed cleaner (aspirator) in a second step (Table 2). This second step resulted in 100% seeds of free threshing phenotype. A closer visual inspection of the free threshing seeds revealed that some of the seeds had a slimmer shape, thus resembling dehulled *T. spelta* grains (25 and 6 seeds in sample 1 and sample 2 respectively, data not shown). This led to the conclusion that a too harsh threshing process partly disrupted some of the pollen parent husks and caused the release of some spelt grains. This finding was confirmed by evaluating the sieving of seeds harvest from pure pollen parent Badenstern or Badenkrone as shown in sample 3 and sample 4 (Table 3). Among the 1877 hulled seeds from *T. spelta* (pollen parent) 30 free threshing grains where found (1.6%). Therefore, sorting a mixture by sieves, aspirator and color sorter would result in a purity rate of 97-98%. This is far above the recommended hybridity of at least 90% (OECD SEED SCHEMES 2014: OECD Schemes for the Varietal Certification or the Control of Seed Moving in International Trade, ANNEX VIII, pages 99-101, OECD 2014, http://www.oecd.org/tad/code/1_complete%20document.pdf).

TABLE 2

Sorting of harvested F1 seed mixtures.
Results of first sieving step, where fraction 2 contained free threshing and hulled types (*), results of second sorting step fraction FT.

| sample | Yield mixture of seed parent and pollen parent (g) | weight of fraction 1 Elements larger than 3.0 mm diameter (hulled seeds) (g) | weight of fraction 2 elements smaller than 3.0 mm diameter (mainly free threshing seeds) (g) | purity of fraction 2* after first step % | weight of fraction FT after second sorting step: elements smaller than 3.0 mm diameter (only free threshing seeds) (g) | purity of fraction FT after second step % |
|---|---|---|---|---|---|---|
| Sample 1 | 245.6 | 178.6 | 67 | 90% | 46 | 97.8% |
| Sample 2 | 124.1 | 108.7 | 15.4 | 90% | 10.2 | 98.5% |

N.b.: at Pochefstroom, TKW was only 26 g, whereas at in Gatersleben TKW was 40.3 g.

TABLE 3

Sorting the pollen parent seed by sieve, wind and color sorter

| sample | Yield of pollen parent (g) | number of hulled seeds | number of free threshing elements | percentage false positives free treshing % |
|---|---|---|---|---|
| Sample 3 | 201 | 1877 | 30 | 1.6% |
| Sample 4 | 49.5 | 515 | 25 | 4.9% |

Thus, by simple sorting techniques it is possible to enrich the fraction of F1 wheat seeds harvested in a mixture to more than 97%.

The invention claimed is:

1. A method of separating hybrid seeds of *durum* wheat from a mixture comprising said hybrid seeds and inbred seeds of said *durum* wheat, comprising:
   (a) providing a mixture of seeds of *durum* wheat, wherein said mixture of seeds has been obtained by interplanting a combination of plants comprising a male sterile or conditionally male sterile seed parent and a male fertile pollen parent, wherein said seed parent and pollen parent produce at least two types of seeds, at least one of which being said hybrid seeds, said at least two types of seed having different phenotypes allowing separation of said hybrid seed with non-invasive methods based on the differences in said phenotypes, said different phenotypes being determined by an allele or a combination of alleles at one or more genetic loci, wherein said allele or combination of alleles at one or more genetic loci are alleles of a Tg gene and a Q gene and the genotype $tgtg^{2B}QQ^{5A}$ produces a free-threshing phenotype; wherein said seed parent is homozygous for a first allele or combination of alleles at said one or more genetic loci resulting in a first phenotype and said pollen parent is homozygous for a second allele or combination of alleles at said one or more genetic loci resulting in a second phenotype; wherein said seed parent is homozygous for one or a combination of alleles at one or more genetic loci, wherein at least one of said alleles in said seed parent is dominant or partially dominant, and said pollen parent is homozygous for one or a combination of alleles at said one or more genetic loci, wherein at least one of said alleles in said pollen parent is recessive or partially recessive; and wherein said combination of plants has (i) said one allele or combination of alleles at one or more genetic loci in said seed parent manifests in seeds with a free-threshing phenotype and wherein said one allele or combination of alleles at one or more genetic loci in said pollen parent manifests in seeds with a hulled phenotype; or (ii) said one allele or combination of alleles at one or more genetic loci in said seed parent manifests in seed with a hulled phenotype and wherein said one allele or combination of alleles at one or more genetic loci in said pollen parent manifests in seeds with a free-threshing phenotype; and
   (b) separating said hybrid seeds using a non-invasive separation method based on differences in size, surface condition, and/or specific weight of the seeds.

2. The method of claim 1, wherein the genes determining said hulled phenotype are recessively inherited.

3. The method of claim 1, wherein said interplanting comprises row or strip planting or mixed interplanting.

4. The method of claim 1, wherein said interplanting comprises sowing the seed of or planting young plants of said seed parent and said pollen parent into the soil.

5. The method of claim 1, further comprising harvesting the seeds produced prior to separating.

6. The method of claim 1, wherein said seed parent is homozygous for one or a combination of alleles at one or more genetic loci, wherein at least one of said alleles in said seed parent is recessive or partially recessive, and said pollen parent is homozygous for one or a combination of alleles at one or more genetic loci, wherein at least one of said alleles in said pollen parent is dominant or partially dominant.

7. The method of claim 6, wherein said combination of plants comprises said one allele or combination of alleles at one or more genetic loci in said seed parent manifests in seeds with a hulled phenotype and wherein said one allele or combination of alleles at one or more genetic loci in said pollen parent manifests in seeds with a free-threshing phenotype.

8. The method of claim 1, wherein the free-threshing phenotype is maternally expressed.

9. A method of separating hybrid seed of *durum* wheat from a mixture of said hybrid seed and inbred seed, comprising: providing said mixture, wherein embryos of said hybrid seeds have a genotype comprising one haploid genome copy of the seed parent and one haploid genome copy of the pollen parent, wherein embryos of said inbred seeds have a genotype comprising two haploid genome copies of the pollen parent, wherein said seed parent is male sterile or conditionally male sterile and wherein said pollen parent is male fertile, wherein (a) said seed parent is homozygous for seed with a free-threshing phenotype and said pollen parent is homozygous for seed with a hulled phenotype, or (b) said seed parent is homozygous for seed with a hulled phenotype and said pollen parent is homozygous for seeds with a free-threshing phenotype; and wherein said free-threshing or hulled phenotype comprises the presence of one or a combination of alleles at one or more genetic loci which are alleles of a Tg gene and a Q gene and the genotype $tgtg^{2B}QQ^{5A}$ produces a free-threshing phenotype; and applying said mixture of seeds to a means for separation according to size, surface condition, and/or specific weight of the seeds.

10. The method of claim 1, wherein the ratio of pollen parent to seed parent is 1:100 to 25:100.

11. The method of claim 1, wherein said seed parent is *Triticum turgidum* L. ssp. *durum Desf.* or *T. turgidum* L. ssp. *parvicoccum*.

12. The method of claim 1, wherein said pollen parent is selected from *T. turgidum* L. ssp. *dicoccum* or *T. turgidum* L. ssp. *dicoccoides*.

13. The method of claim 9, wherein the genes determining said hulled phenotype are recessively inherited.

14. The method of claim 1, wherein male sterility is based on cytoplasmic male sterility, nuclear male sterility or a trait introduced into said plant by genetic engineering or mutation; or is induced using a gametocide.

15. A hybrid *durum* wheat seed produced by the method of claim 1.

16. The method of claim 9, wherein the free-threshing phenotype is maternally expressed.

* * * * *